United States Patent [19]

Burba, III

[11] 4,430,097

[45] * Feb. 7, 1984

[54] LITHIUM ALUMINATES FOR SEPARATING HYDROCARBONS

[75] Inventor: John L. Burba, III, Angleton, Tex.

[73] Assignee: The Dow Chemical Co., Midland, Mich.

[*] Notice: The portion of the term of this patent subsequent to Mar. 23, 1999 has been disclaimed.

[21] Appl. No.: 360,702

[22] Filed: Mar. 22, 1982

Related U.S. Application Data

[63] Continuation-in-part of Ser. No. 217,613, Dec. 18, 1980, Pat. No. 4,321,065.

[51] Int. Cl.$^3$ ............................................. B01D 15/08
[52] U.S. Cl. .......................................... 55/67; 55/74; 55/386; 210/656
[58] Field of Search ..................... 55/74, 75, 389, 67, 55/386; 210/656; 252/184

[56] References Cited

U.S. PATENT DOCUMENTS

| | | | |
|---|---|---|---|
| 4,257,885 | 3/1981 | Grose et al. | 55/75 |
| 4,313,015 | 1/1982 | Broughton | 55/75 |
| 4,321,065 | 3/1982 | Burba | 55/67 |
| 4,348,297 | 9/1982 | Bauman et al. | 55/386 X |

*Primary Examiner*—John Adee
*Attorney, Agent, or Firm*—W. J. Lee

[57] ABSTRACT

Particles of crystalline LiX·2Al(OH)$_3$·$n$H$_2$O, where X is a monovalent, divalent, or trivalent anion, especially chlorine, are useful in separating hydrocarbons according to boiling point ranges.

10 Claims, No Drawings

LITHIUM ALUMINATES FOR SEPARATING HYDROCARBONS

CROSS REFERENCE TO RELATED APPLICATION

This is a continuation-in-part of application Ser. No. 217,613, filed Dec. 18, 1980, now U.S. Pat. No. 4,321,069.

BACKGROUND OF THE INVENTION

U.S. Pat. Nos. 4,116,856; 4,116,858; 4,159,311; and 4,221,767 show the preparation of crystalline lithium aluminates by reacting of lithium compounds with hydrous alumina under certain conditions. The so-prepared aluminates are useful in selectively removing Li+ ions from aqueous solutions. The crystalline aluminates are identified, generally, by the empirical formula $LiX\cdot 2Al(OH)_3$ where X is a halogen of the group chlorine, bromine, or iodine, especially chlorine. It is realized, of course, that there are waters of hydration accompanying the aluminate crystals. It is also known that $Al_2O_3$ is used as a packing material for gas chromatograph columns.

It has now been found that lithium aluminates such as are made in accordance with the above named patents and by other techniques discussed hereinafter, are useful in separating hydrocarbon fractions carried in a gas stream especially when the aluminates are not deposited within, or upon, a particulate substrate.

SUMMARY OF THE INVENTION

Lithium aluminates, especially crystalline $LiCl\cdot 2Al(OH)_3\cdot nH_2O$, are effective as a packing material in a vessel or column, for separating gaseous mixtures of hydrocarbons into fractions according to boiling point ranges.

DETAILED DESCRIPTION OF THE INVENTION

The lithium aluminates for use in the present invention are prepared, in general, by combining appropriate lithium compounds with hydrous alumina and, by application of elevated temperature, forming lithium aluminates wherein the lithium salt is deposited within and between the layers of the aluminum hydroxide crystal.

The hydrous alumina with which one begins may be hydrous, amorphous alumina, e.g., freshly prepared $Al(OH)_3$ or may be crystalline hydrous alumina, such as norstrandite, bayerite, gibbsite or mixtures of these.

The lithium compound for reaction with (or intercalation within) the hydrous alumina structure may be LiX, where X is an acid forming anion, such as halogen, especially chlorine, inorganic, organic, or hydroxyl.

The number of intercalation layers in the hydrous alumina structure which receives the lithium salt will depend, largely, on the heat history, the origin, and/or the environment in which the hydrous alumina crystal is formed. If the crystal is formed within the close confines of a reticular resin or other support, the crystal aggregates are likely to be smaller than when the crystal is formed in neat fashion without being confined. It is within the purview of the present invention to have the hydrous aluminate supported on, or within, a particulate substrate but such substrate may limit the application to only those hydrocarbons which are substantially inert to the substrate. Unsupported aluminates of this invention generally have larger crystal aggregates (i.e., larger particle size) and also are not so limited in their application to the separation of hydrocarbons.

The lithium aluminates discussed here have two crystal structures, viz those of 2-layer crystallographic unit cells and those of 3-layer crystallographic unit cells. The 3-layer lithium aluminates have a 3-fold screw axis oriented parallel to the c-axis of the lithium aluminate crystal. The 2-layer lithium aluminates have a 2-fold axis of rotation oriented parallel to the c-axis. The 2-layer variety is uniquely prepared by reacting a lithium salt (excluding LiOH) with gibbsite, whereas the 3-layer variety is prepared by reacting a lithium salt with another form of hydrous alumina such as bayerite or norstrandite.

It will be understood, of course, that a given discrete particle of lithium aluminate will be an aggregation or "stack" of many crystals, and when prepared in neat form, rather than confined within the pores of a resin or other support, can be as large as about $10^{-2}$ mm in size. It is best if the lithium aluminate particles are fine enough to pass through a 70-mesh screen, preferably fine enough to pass through a 100-mesh screen.

Preparation of the lithium aluminates may comprise, but is not limited to, any of the following:

1. Reacting amorphous $Al(OH)_3$ with a lithium salt (in aq. solution), especially LiCl, at a temperature high enough to form crystalline $LiX\cdot 2Al(OH)_3\cdot nH_2O$, where X is an anion. Ordinarily, temperatures of about 40° C. to about 100° C. are used. The number of waters of hydration ($nH_2O$) is not especially critical and the stoichiometric numerical value of n is generally in the range of about 1 to 6;

2. Reacting crystalline hydrous alumina, such as bayerite, norstrandite, gibbsite, and the like, with aqueous LiOH to form crystalline $LiOH\cdot 2Al(OH)_3\cdot nH_2O$ which may be used as is or may be reacted with LiCl to form crystalline $LiCl\cdot 2Al(OH)_3\cdot nH_2O$ or with other Li salts to form other lithium aluminates, $LiX\cdot 2Al(OH)_3\cdot nH_2O$, where X is a monovalent anion, divalent anion, or trivalent anion;

3. Reacting crystalline hydrous alumina, such as bayerite, norstrandite, gibbsite and the like, with concentrated (>12% by wt.) LiCl at a high temperature of about 85° C.–125° C. to form crystalline $LiCl\cdot 2Al(OH)_3\cdot nH_2O$; or 4. Reacting crystalline $LiOH\cdot 2Al(OH)_3\cdot nH_2O$ or crystalline $LiCl\cdot 2Al(OH)_3\cdot nH_2O$ with aqueous solutions of inorganic acids or organic acids, or soluble, ionizable metal salts of such acids, to cause the anions of such acids to replace at least a portion of the anions in the crystal, thereby forming crystalline $LiX\cdot 2Al(OH)_3\cdot nH_2O$ where X is a monovalent, divalent, or trivalent anion of such acid or metal salt of such acid.

The hydrocarbons which are of interest in the present invention are those which have components with unequal boiling points and includes, e.g., substituted and/or unsubstituted mixtures of alkyls, aryls, alkaryls, aralkyls, naphthyls, alkylenes, arylenes, and naphthylenes. Mixtures of halocarbons, including those which contain perhalogens, such as $CCl_4$, are of interest.

Mixtures of substituted and/or unsubstituted liquid hydrocarbons having components with a boiling range up to about 400° C. are of interest. Appreciably effective component separation is usually achieved between components with different boiling points on a qualitative basis.

Operation of the gas chromatograph is in accordance with the usual techniques, except of course that the packing in the column is one of the crystalline LiX.2Al(OH)$_3$.$n$H$_2$O compounds of the present invention. A sample of the hydrocarbon mixture to be analyzed is injected into the inert gas carrier which carries it through the packed column where the various components are adsorbed and desorbed at different rates, depending on their boiling points.

For instance, in gas chromatography a sample is injected into a packed column which is built into a furnace. The liquid samples are flashed to vapors and carried through the column with an inert gas such as He. After passing through the column, the gasses pass through a thermal conductivity cell where they are detected. The data is represented by means of a strip chart recorder. The gas chromatograph used in these experiments could not collect samples, so separate analysis of components was not done. Instead, the components were identified by their holdup times in the column, as determined from one-component experiments.

The separation of hydrocarbons is not limited to simply that performed in a gas chromatograph for analytical purposes. Vessels or columns much larger than a chromatograph column may be used wherein an inert gas carrier is used to carry entrained or vaporous hydrocarbon mixtures through the lithium aluminate particles, thereby effecting a separation of the hydrocarbon mixture into components.

Example 1

A gas chromatography column 4' long and 0.25" in diameter is packed with 3-layer LiCl.2Al(OH)$_3$.$n$H$_2$O screened to a mesh size passing through a 100 mesh screen (U.S. Standard Sieve size). The specific surface area of the 3-layer aluminate is in the range of about 1-3 sq. meter/gm.

The column is placed in a gas chromatograph apparatus having a programmable heating rate. A mixture of organic compounds having the following composition is injected into the column: 1.67 wt. % methylene chloride, 1.78 wt. % chloroform, 1.60 wt. % carbontetrachloride, 1.32 wt. % benzene, 2.29 wt. % toluene, and 1.34 wt. % ethylbenzene in carbon disulfide.

The injection and detector temperatures are at 300° C., the flow rate of He is 30 cc/min., and the temperature program is 70° C. to 250° C. at a rate of 16° c/min. The initial holdup, methylene chloride, is 2 minutes.

The peaks on the strip chart recorder are very sharp and symmetrical, with base-line separations of all components except for the methylene chloride/chloroform and the benzene/toluene peaks. Each of the seven components exhibit definite, identifiable peaks.

Example 2

The above example is repeated, using 2-layer LiCl.2Al(OH)$_3$.$n$H$_2$O and similar results are obtained.

Example 3

Example 1 is repeated except that the mesh size of the LiCl.2Al(OH)$_3$.$n$H$_2$O is that which passes through a 70-mesh screen and is retained on a 100-mesh screen. The results are generally good, but there is some loss of resolution of the chlorocarbon compounds.

I claim:

1. In a process for separating hydrocarbon mixtures, carried in an inert gaseous carrier, into components the use of crystalline LiX.2AL(OH)$_3$.$n$H$_2$O, where X is a monovalent, divalent, or trivalent anion and n is an integer having a numerical value in the range of about 1 to about 6, as a packing material in a contacting vessel.

2. The crystalline LiX.2Al(OH)$_3$.$n$H$_2$O of claim 1 wherein X is a monovalent, divalent, or trivalent anion selected from the group consisting of halide, inorganic acid radical, hydroxyl, and organic radical, and where n is from about 1 to about 6.

3. The crystalline LiX.2Al(OH)$_3$.$n$H$_2$O of claim 1 wherein X is chlorine and n is from about 1 to about 6.

4. The packing material of claim 1 wherein the particles are fine enough to pass through a 70-mesh screen.

5. The packing material of claim 1 wherein the particles are fine enough to pass through a 100-mesh screen.

6. The packing material of claim 1 wherein the particles have a surface area in the range of about 1 meters$^2$ per gm to about 3 meters$^2$ per gm.

7. The process of claim 1 wherein the hydrocarbon mixtures comprise liquid hydrocarbons having components of unequal boiling points.

8. The process of claim 1 wherein the hydrocarbon mixture comprises liquid halocarbon compounds having components of unequal boiling points.

9. The process of claim 1 wherein the hydrocarbon mixture comprises at least two of the class consisting of aliphatic hydrocarbons, aromatic hydrocarbons, and halocarbons.

10. A process for separating a hydrocarbon mixture into components, said process comprising
 providing a vessel or column containing particulate crystalline LiX.2Al(OH)$_3$.$n$H$_2$O, where X is a monovalent, divalent, or trivalent anion and n is an integer having a numerical value in the range of about 1 to about 6,
 said vessel or column being adapted for the flow of gas-entrained fluids therethrough,
 entraining said hydrocarbon mixture in an inert gas carrier,
 passing the so-entrained mixture through the vessel, and
 collecting the effluent from the vessel in component fractions.

* * * * *

UNITED STATES PATENT AND TRADEMARK OFFICE
CERTIFICATE OF CORRECTION

PATENT NO. : 4,430,097

DATED : February 7, 1984

INVENTOR(S) : John L. Burba, III

It is certified that error appears in the above—identified patent and that said Letters Patent is hereby corrected as shown below:

Col. 1, line 9 "4,321,069" should be --4,321,065--.

Signed and Sealed this

Twenty-fourth Day of July 1984

[SEAL]

Attest:

GERALD J. MOSSINGHOFF

Attesting Officer           Commissioner of Patents and Trademarks